US00PP29148P3

(12) United States Plant Patent
Svenson

(10) Patent No.: US PP29,148 P3
(45) Date of Patent: Mar. 27, 2018

(54) ***PIERIS* PLANT NAMED 'SINCERE'**

(50) Latin Name: *Pieris japonica*
Varietal Denomination: Sincere

(71) Applicant: Sven E. Svenson, Salem, OR (US)

(72) Inventor: Sven E. Svenson, Salem, OR (US)

( * ) Notice: Subject to any disclaimer, the term of this patent is extended or adjusted under 35 U.S.C. 154(b) by 34 days.

(21) Appl. No.: 14/999,744

(22) Filed: Jun. 22, 2016

(65) Prior Publication Data

US 2016/0381847 P1 Dec. 29, 2016

Related U.S. Application Data

(60) Provisional application No. 62/231,057, filed on Jun. 23, 2015.

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Keith O Robinson
(74) *Attorney, Agent, or Firm* — C. A. Whealy

(57) ABSTRACT

A new and distinct cultivar of *Pieris* plant named 'Sincere', characterized by its compact and upright plant habit; freely branching habit; leaves that are initially red purple in color and with development become green in color; inflorescences that are upright to drooping in aspect; deep red purple-colored flower buds; relatively late flowering response; numerous white-colored flowers; and good garden performance.

2 Drawing Sheets

Botanical designation: *Pieris japonica.*
Cultivar denomination: 'SINCERE'.

BACKGROUND OF THE INVENTION

The present Invention relates to a new and distinct cultivar of *Pieris* plant, botanically known as *Pieris japonica*, and hereinafter referred to by the name 'Sincere'.

The new *Pieris* plant is a product of a planned breeding program conducted by the Inventor in Hopewell, Oreg. The objective of the breeding program is to develop new compact and freely-branching *Pieris* plants with stable and attractive flower color and good garden performance.

The new *Pieris* plant originated from a cross-pollination made by the Inventor in March, 1998, in Hopewell, Oreg., of *Pieris japonica* var. *japonica* 'Valley Valentine', not patented, as the female, or seed, parent with an unnamed seedling selection of *Pieris japonica*, not patented, as the male, or pollen, parent. The new *Pieris* plant was discovered and selected by the Inventor as a single flowering plant within the progeny of the stated cross-pollination in a controlled outdoor nursery environment in Hopewell, Oreg. in early March, 2003.

Asexual reproduction of the new *Pieris* plant by cuttings propagated in a controlled environment in Hopewell, Oreg. since 2003 has shown that the unique features of this new *Pieris* plant are stable and reproduced true to type in successive generations.

SUMMARY OF THE INVENTION

Plants of the new *Pieris* have not been observed under all possible combinations of environmental conditions and cultural practices. The phenotype may vary somewhat with variations in environmental conditions such as temperature, length of growing season and/or light intensity without, however, any variance in genotype. The following traits have been repeatedly observed and are determined to be the unique characteristics of 'Sincere'. These characteristics in combination distinguish 'Sincere' as a new and distinct *Pieris* plant:

1. Compact and upright plant habit.
2. Freely branching habit.
3. Leaves that are initially red purple in color and with development become green in color.
4. Inflorescences that are upright to drooping in aspect.
5. Deep red purple-colored flower buds.
6. Relatively late flowering response.
7. Numerous white-colored flowers.
8. Good garden performance.

Plants of the new *Pieris* differ primarily from plants of the female parent, 'Valley Valentine', in the following characteristics:

1. Plants of the new *Pieris* are taller than plants of 'Valley Valentine'.
2. Plants of the new *Pieris* are more freely branching than plants of 'Valley Valentine'.
3. Plants of the new *Pieris* retain leaves for a longer period of time than plants of 'Valley Valentine'.
4. Developing leaves of plants of the new *Pieris* are red purple in color whereas developing leaves of plants of 'Valley Valentine' are greyed orange in color.
5. Inflorescences of plants of the new *Pieris* are more upright than inflorescences of plants of 'Valley Valentine'.
6. Plants of the new *Pieris* flower later than plants of 'Valley Valentine'.
7. Plants of the new *Pieris* are more freely flowering than plants of 'Valley Valentine'.

Plants of the new *Pieris* differ primarily from plants of the male parent selection in the following characteristics:

1. Developing leaves of plants of the new *Pieris* are red purple in color whereas developing leaves of plants of the male parent selection are greyed orange in color.
2. Flower buds of plants of the new *Pieris* are deep red purple in color whereas flower buds of plants of the male parent selection are yellow green in color.
3 Sepals, peduncles and pedicels of plants of the new *Pieris* are deep red purple in color whereas sepals, peduncles and pedicels of plants of the male parent selection are yellow green in color.

Plants of the new *Pieris* can be compared to the plants of the *Pieris japonica* 'Katsura', disclosed in U.S. Plant Pat. No. 15,452. In side-by-side comparisons conducted in Hopewell, Oreg., plants of the new *Pieris* differed from plants of 'Katsura' in the following characteristics:

1. Plants of the new *Pieris* were taller than plants of 'Katsura'.
2. Developing leaves of plants of the new *Pieris* were red purple in color whereas developing leaves of plants of 'Katsura' were greyed purple in color.
3. Leaves of plants of the new *Pieris* were longer and broader than leaves of plants of 'Katsura'.
4. Plants of the new *Pieris* flowered later and flowers lasted for a longer period of time than plants of 'Katsura'.
5. Inflorescences of plants of the new *Pieris* were longer than inflorescences of plants of 'Katsura'.
6. Flower petals of plants of the new *Pieris* were white in color whereas flower petals of plants of 'Katsura' were greyed purple in color.
7. Sepals, peduncles and pedicels of plants of the new *Pieris* were red purple in color whereas sepals, peduncles and pedicels of plants of 'Katsura' were greyed purple in color.

BRIEF DESCRIPTION OF THE PHOTOGRAPHS

The accompanying colored photographs illustrate the overall appearance of the new *Pieris* plant showing the colors as true as it is reasonably possible to obtain in colored reproductions of this type. Colors in the photographs may differ slightly from the color values cited in the detailed botanical description which accurately describe the colors of the new *Pieris* plant.

The photograph on the first sheet is a close-up view of typical developing leaves, developed leaves and inflorescences of 'Sincere'.

The photograph on the second sheet is a close-up view of typical developed leaves and inflorescences of 'Sincere'.

DETAILED BOTANICAL DESCRIPTION

The aforementioned photographs and following observations and measurements describe plants grown in ground beds in an outdoor nursery in Hopewell, Oreg. and under cultural practices typical of commercial production. Plants used for the photographs and description were seven years old. In the following description, color references are made to The Royal Horticultural Society Colour Chart, 2001 Edition, except where general terms of ordinary dictionary significance are used.

Botanical classification: *Pieris japonica* 'Sincere'.

Parentage:

*Female, or seed, parent.*—*Pieris japonica* 'Valley Valentine', not patented.

*Male, or pollen, parent.*—Unnamed seedling selection of *Pieris japonica*, not patented.

Propagation:

*Type.*—By stem cuttings.

*Time to initiate roots, autumn and winter.*—About seven weeks at temperatures about 20° C.

*Root description.*—Fine, fibrous; white to light brown in color.

*Rooting habit.*—Moderate branching; medium density.

Plant description:

*Plant and growth habit.*—Woody perennial, evergreen; compact, upright to outwardly spreading plant habit; oval in overall shape; vigorous growth habit.

*Branching habit.*—Freely branching habit with typically about three to four lateral branches bypassing each terminal inflorescence; if terminal inflorescences removed, up to six lateral branches will develop.

*Plant height, soil level to top of flowers.*—About 400 cm.

*Plant diameter, area of spread.*—About 150 cm.

*Lateral branch description.*—Length: About 7 cm to 12 cm. Diameter: About 2 mm to 4 mm. Internode length: About 2 mm to 5 mm. Strength: Strong. Texture: Smooth, glabrous. Color: Close to between 144B and 144C.

*Leaf description.*—Arrangement: Whorled at terminals; simple. Length: About 6 cm to 8 cm. Width: About 1.5 cm to 2 cm. Shape: Elliptic to oblanceolate. Apex: Acute. Base: Attenuate. Margin: Towards the base, entire; towards the apex, crenate. Venation pattern: Pinnate. Texture, upper and lower surfaces: Smooth, glabrous. Color: Developing leaves, upper and lower surfaces: Close to between 59A and 60B. Fully expanded leaves, upper surface: Close to N137D; venation, close to 144A. Fully expanded leaves, lower surface: Close to between 144A and 144B; venation, close to 144C. Petioles: Length: About 5 mm to 8 mm. Diameter: About 1 mm to 3 mm. Texture, upper and lower surfaces: Smooth, glabrous. Color, upper surface: Close to 60B to 60C fading to 144B. Color, lower surface: Close to 144B to 144C.

Flower description:

*Flower arrangement and appearance.*—Single urceolate flowers arranged in terminal paniculate racemes; developing inflorescences initially upright, then becoming more horizontal and then bending downwardly with the increasing weight of developing flowers.

*Flowering habit.*—Freely flowering habit; about 120 to 380 flowers develop per inflorescence during the flowering period.

*Natural flowering season.*—Relatively late flowering response; plants of the new *Pieris* typically flower from early March to mid-April in Hopewell, Oreg.

*Flower longevity.*—Individual flowers last about 18 to 45 days on the plant.

*Fragrance.*—Sweet, pleasant.

*Inflorescence length.*—About 9 cm to 25 cm.

*Inflorescence diameter.*—About 8 cm to 18 cm.

*Flower diameter.*—About 5 mm to 7 mm.

*Flower depth.*—About 6 mm to 8 mm.

*Flower buds.*—Length: About 4 mm to 6 mm. Diameter: About 3 mm to 5 mm. Shape: Ovoid. Color: Close to between 60C to 60D.

*Petals.*—Arrangement: Single urceolate flower form; single whorl of five petals fused at the base. Length: About 8 mm. Width: About 2 mm. Shape: Ovate with obtuse apex. Margin: Entire. Texture, upper and lower surfaces: Smooth, glabrous. Color: When opening, upper and lower surfaces: Close to NN155D. Fully opened, upper and lower surfaces: Close to NN155D.

*Sepals.*—Arrangement: Five fused in a single whorl. Length: About 2 mm to 4 mm. Width: About 1 mm to 2 mm. Shape: Ovate. Apex: Acute. Base: Cuneate to broadly cuneate. Texture, upper and lower surfaces: Smooth, glabrous. Color: Immature, upper and lower surfaces: Close to 60B to 60C. Mature, upper and lower surfaces: Close to 60B to 60C; towards the apex, fading to close to 155A.

*Peduncles.*—Length: About 8 cm to 12 cm. Diameter: About 1 mm to 3 mm. Angle: Initially upright to about 80° from vertical. Strength: Moderately strong. Texture: Smooth, glabrous. Color: Close to 60A to 60B.

*Pedicels.*—Length: About 3 mm to 6 mm. Diameter: About 1 mm to 2 mm. Angle: About 40° to 80° from vertical. Strength: Moderately strong. Texture: Smooth, glabrous. Color: Close to 60B to 60C.

*Reproductive organs.*—Androecium: Quantity per flower: About ten. Anther shape: Oval. Anther length: About 1 mm. Anther color: Close to 200A. Pollen amount: Scarce. Pollen color: Close to 167C. Gynoecium: Quantity of pistils per flower: Typically one. Pistil length: About 4 mm to 6 mm. Style length: About 4 mm to 5 mm. Style color: Close to NN155D. Stigma shape: Narrowly club-shaped. Stigma diameter: Less than 1 mm. Stigma color: Close to NN155D. Ovary color: Close to NN155D.

*Seeds and fruits.*—Seed and fruit development have not been observed on plants of the new *Pieris*.

Garden performance: Plants of the new *Pieris* have been observed to have good garden performance and to be tolerant to rain, wind, ice to 1.5 cm in thickness, snow to 8 cm in thickness and temperatures from about −19° C. to about 42° C.

Disease & pest resistance: Plants have not been observed to be resistant to pathogens and pests common to *Pieris* plants.

It is claimed:

1. A new and distinct cultivar of *Pieris* plant named 'Sincere' as illustrated and described.

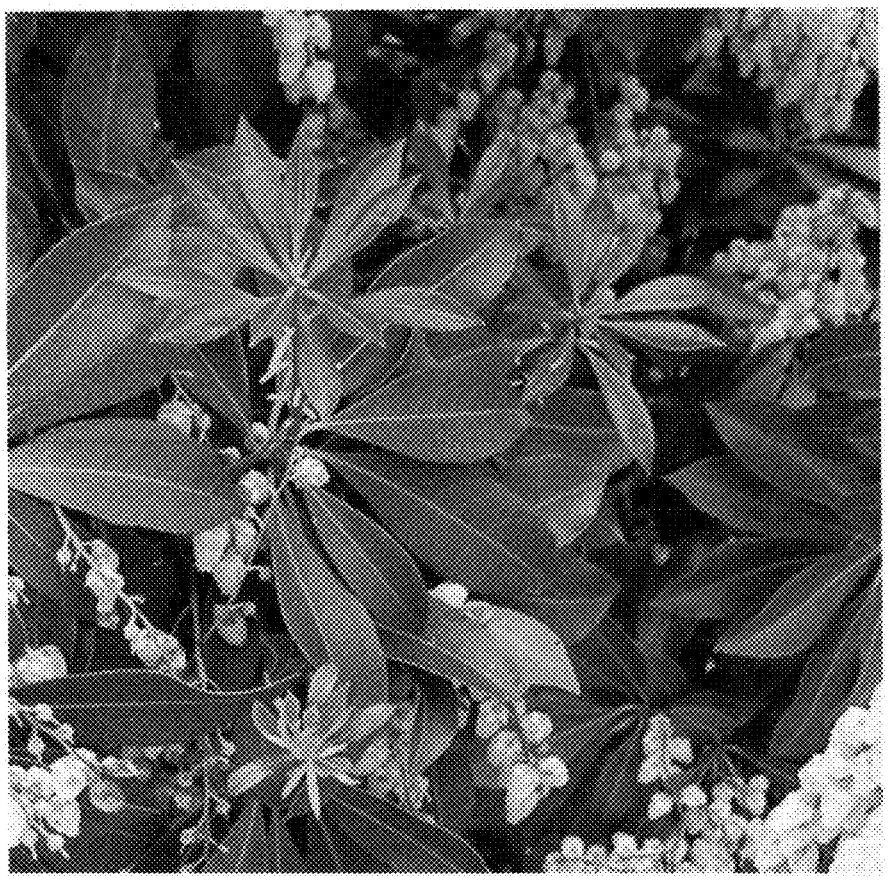

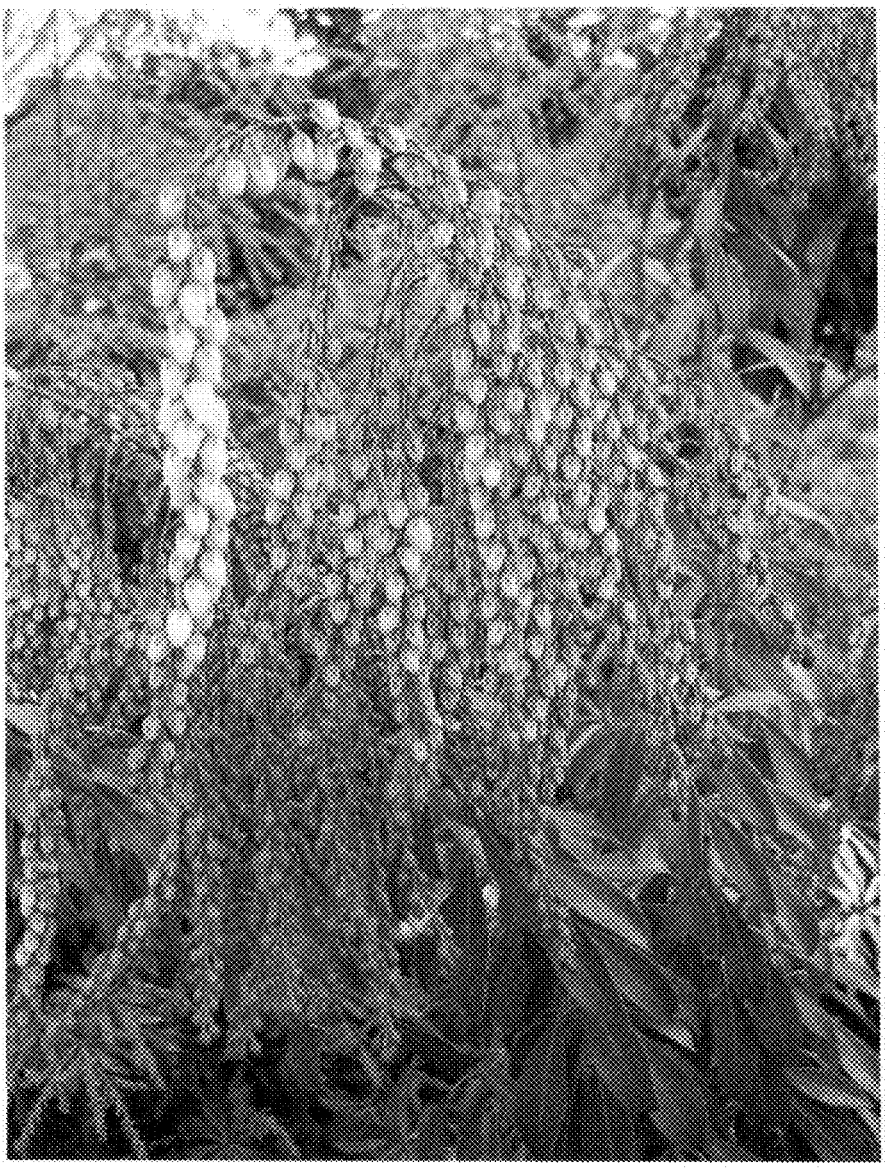

* * * * *